United States Patent [19]

Tomcufcik et al.

[11] Patent Number: 5,079,247
[45] Date of Patent: Jan. 7, 1992

[54] N¹-SUBSTITUTED BENZ(CD)INDOL-2-IMINE COMPOUNDS AS CARDIOVASCULAR AGENTS

[75] Inventors: Andrew S. Tomcufcik, Old Tappan, N.J.; Walter E. Meyer, Suffern; Nancy H. Eudy, Cornwall, both of N.Y.

[73] Assignee: American Cyanamid Company, Stamford, Conn.

[21] Appl. No.: 495,815

[22] Filed: Mar. 14, 1990

[51] Int. Cl.⁵ .................... C07D 403/12; A61K 31/45
[52] U.S. Cl. .................... 514/232.8; 514/318; 514/323; 514/333; 514/339; 514/397; 544/124; 544/139; 546/193; 546/200; 546/256; 546/272; 548/336
[58] Field of Search .............. 514/232.8, 318, 323, 514/333, 339, 397; 544/124, 139; 546/193, 200, 256, 272; 548/336

[56] References Cited

U.S. PATENT DOCUMENTS 4,261,896  4/1981  Tomcufcik ..................... 260/326.9
4,728,663  3/1988  Tomcufcik ..................... 514/394

OTHER PUBLICATIONS

Chemical Abstracts, vol. 108, No. 5, Abstract 37,830v, p. 639, Feb. 1, 1988, Tomcufcik et al.

Primary Examiner—Jane T. Fan
Assistant Examiner—Zinna Northington-Davis
Attorney, Agent, or Firm—Thomas S. Szatkowski

[57] ABSTRACT

N¹ substituted benz [cd] indol -2(1H)-imines useful as inhibitors of Thromboxane synthetase enzyme, hypertension and arrhythmia are described.

43 Claims, No Drawings

N[1]-SUBSTITUTED BENZ(CD)INDOL-2-IMINE COMPOUNDS AS CARDIOVASCULAR AGENTS

This invention relates to new organic compounds and, more particularly, is concerned with novel substituted benz[cd]indol-2-(1H)-imines which may be represented by the following structural formal:

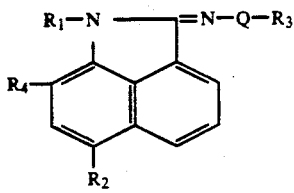

wherein $R_1$ is selected from the group consisting of alkyl $C_1$–$C_6$, phenyl, phenylalkyl ($C_1$–$C_3$), phenylalkoxy ($C_1$–$C_3$),

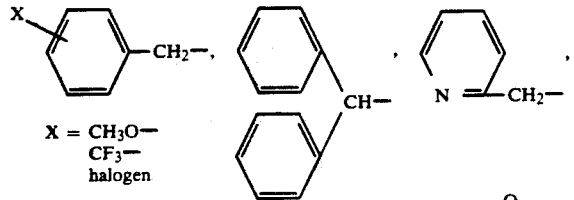

X = CH$_3$O—
CF$_3$—
halogen

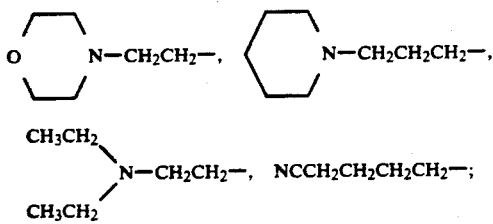

$R_2$ is selected from the group consisting of hydrogen, HO—CH$_2$— or halogen; Q is selected from the group consisting of —(CH$_2$)$_n$—, where n is an integer 1–4, straight or branched chain alkyl $C_1$–$C_4$; $R_3$ is selected from either

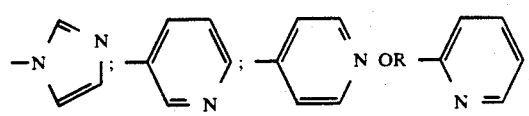

$R_4$ is selected from hydrogen or methyl; and the pharmacologically acceptable salts thereof.

The organic bases of this invention form non-toxic acid-addition salts with a variety of pharmacologically acceptable organic and inorganic salt-forming reagents. Thus acid-addition salts, formed by admixture of the organic free base with one or more equivalents of an acid, suitably in a neutral solvent, are formed with such acids as sulfuric, phosphoric, hydrochloric, hydrobromic, hydriodic, sulfamic, citric, lactic, malic, succinic, maleic, fumaric, tartaric, acetic, benzoic, gluconic, ascorbic and the like. For the purpose of this invention the free bases are equivalent to their non-toxic acid-addition salts.

DETAILED DESCRIPTION OF THE INVENTION

The compounds of the present invention may be readily prepared according to the following reaction scheme, wherein $R_1$, $R_2$, $R_3$ and Q are as described hereinabove.

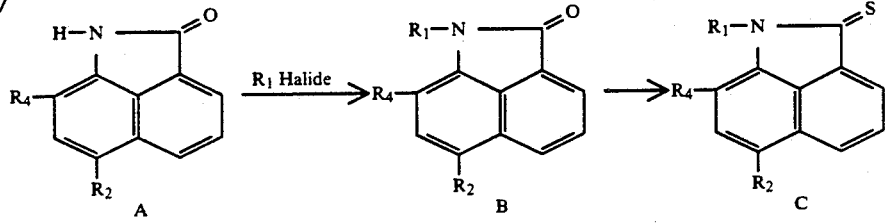

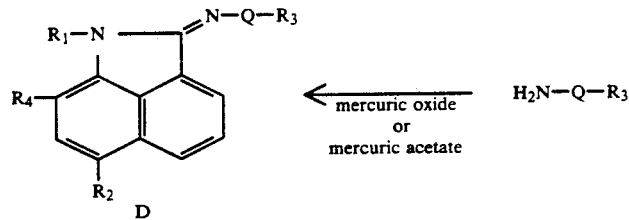

A benz[cd]indol-2-(H)one or substituted benz[cd]indol-2(1H)-one (A) is dissolved in a solvent such as dimethylformamide, is treated portionwise with sodium hydride in mineral oil and then with an $R_1$ halide, heated, cooled, diluted with water, and concentrated. The reaction mixture is extracted with chloroform or methylene chloride, the solution is then passed thru hydrous magnesium silicate, and concentrated giving the appropriate 1-substituted benz[cd]indol-2-(1H)-ones (B) where $R_1$, $R_2$ and $R_4$ are as described above. The compound (B) is dissolved in a solvent such as dioxane or pyridine and refluxed with phosphorus pentasulfide. The reaction mixture is poured into a large volume of boiling water, heated, and allowed to cool with vigorous stirring. The solid is collected giving 1-substituted benz[cd]indole-2(1H)-thiones (C), where $R_1$, $R_2$ and $R_4$ are as described above. The above thione (C) and the appropriate $R_3$ —Q amine (i.e., 1H-imidazole-1- propanamine, 1H-imidazole-1-butanamine 2(2-pyridine)ethanamine, (3-pyridine)ethanamine, (3-pyridine)butanamine, (4-pyridine)butanamine, etc.) in a suitable solvent such as ethyl alcohol dimethylformamide or 2-methoxyethanol are treated with mercuric oxide or mercuric acetate at reflux temperature for several hours giving the desired compounds (D).

The compounds of this invention inhibit thromboxane synthetase enzyme. Thus, these compounds are useful in the treatment of diseases characterized by an imbalance of thromboxane $A_2$/prostacyclin such as ischemic heart disease, transient ischemic attack, thrombosis and migraine. Recent reviews have established the role of the thromboxane/prostacyclin balance in the vascular system [*Cardiovascular Diseases: New Trends in Surgical and Medical Aspects*, H. Barnett, P. Paoletti, E. Flamm and G. Brambilla, eds., Elesevier/North-Holland Biomedical Press, pp 137-150 (1987)]. Prostacyclin ($PGI_2$) is a potent vasodilator and platelet aggregation inhibitor, whereas thromboxane ($TXA_2$) is a powerful vasoconstrictor and causative of platelet aggregation. $TXA_2$ is synthesized by thromboxane synthetase enzyme located in, for example, blood platelets. When $TXA_2$ production is increased relative to $PGI_2$, platelet aggregation, thrombosis and vasopasm may occur [*Lancet*, 1216 (1977); *Lancet*, 479 (1977); *Science*, 1135 (1976); *Amer. J. Cardiology*, 41 787 (1978)]. $TXA_2$ synthetase inhibitors have been shown to have superior anti-thrombotic action to that of aspirin [*J. Clin. Invest.*, 65 400 (1980); *Br. J Pharmac.*, 76, 3(1982)].

The role of prostaglandins including $TXA_2$ and $PGI_2$ in ischemic heart patients has been reviewed [*Cardiovascular Pharmacology of the Prostaglandins*, A. G. Herman, P. M. Vanhoute, H. Denolin and A. Goosens, eds., Raven Press, New York, pp 361-374 (1982)]. Injection of $TXA_2$ into coronary arteries of guinea pigs and rabbits causes myocardial ischemia and subendocardial necrosis [*Drugs of the Future*, 7, 331 (1982); *Proc. Jao. Acad.*, 53(B), 38 (1977); *Eur. J. Pharmacol.*, 53 49(1978)]. Recent research has demonstrated the beneficial effects of $PGI_2$ and selective inhibition of thromboxane synthetase on ischemic myocardium in canines [*J. Cardiovascular Pharmacology*, 4, 129 (1982)]. Thus compounds which selectively inhibit thromboxane synthetase (and hence $TXA_2$) without adversely affecting $PGI_2$ are useful in the treatment of vascular diseases such as ischemia and migraine. In addition, inhibition of $TXA_2$ formation may effectively treat platelet aggregation and prevent thrombosis.

Under urethan anethesia, 10 μl of arterial blood from Okamoto-Aoki spontaneously hypertensive rats (SHR) (Taconic Farms, Germantown, New York) between 19 and 24 weeks in age was collected in 1 ml of 3.2% sodium citrate in a polystyrene tube. The blood was diluted with 3 ml of cold saline and centrifuged at room temperature for 15 minutes at 460Xg. The platelet rich plasma (PRP) was separated. The platelets were isolated by centrifuging the PRP for 10 minutes at 1060Xg and were washed in 4 ml of cold oxygenated Krebs phosphate buffer, pH 7.4. The chilled platelets, recovered from centrifuging at 800Xg for 10 minutes, were resuspended in oxygenated Krebs phosphate buffer and diluted to contain $4.5-6.0 \times 10^4$ platelets/μl.

The inhibition of thromboxane (TX) formation was studied by determining the concentration of thromboxane $B_2$ ($TXB_2$), the stable hydrolysis product of $TXA_2$. Assay samples, prepared on ice, contained 200 μl platelet suspension, 50 μl saline, and 50 μl vehicle or drug under study at a concentration of $1 \times 10^{-4}M$. The samples were incubated for 10 minutes at 37° C. in metabolic shaker. The reaction was terminated by immersing the tubes in an ice bath and adding 50 μl of 0.5M citric acid. The samples were centrifuged for 10 minutes in a refrigerated centrifuge and the supernatants thus obtained were decanted and stored at $-20°$ C. The $TXB_2$ content for each sample was determined by a direct radioimmunoassay (RIA) utilizing a $TXB_2$ specific RIA kit purchased from New England Nuclear, Boston, Massachusetts and expressed as pg $TXB_2$ formed minute$^{-1}$ sample$^{-1}$, from which the percent inhibition of $TXB_2$ formation was calculated. The results of this test on representative compounds of this invention appear in Table I below.

TABLE I

Thromboxane Synthetase Enzyme Inhibition

| Compound | Example No. | Concentration (M) | % Inhibition |
|---|---|---|---|
| N-[1-(Phenylmethyl)benz[cd]indol-2(1H)-ylidene]-1H-imidazole-1-propanamine, (E)-2-butenedioate (1:2) | 6 | $1 \times 10^{-4}$ | 90 |
| N-[1-(Diphenylmethyl)benz[cd]indol-2(1H)-ylidene]-1H-imidazole-1-propanamine | 7 | $1 \times 10^{-4}$ | 75 |
| N-[1-[2-(4-Morpholinyl)ethyl]-benz[cd]indol-2(1H)-ylidene]-1H-imidazole-1-propanamine, (E)-2-butenedioate (1:2) | 8 | $1 \times 10^{-4}$ | 96 |
| N-[1-(3-Phenoxypropyl)benz[cd]indol-2(1H)-ylidene]-1H-imidazole-1-propanamine, dihydrochloride | 12 | $1 \times 10^{-4}$ | 90 |
| N-[1-(3-Phenylpropyl)benz[cd]indol-2(1H)-ylidene]-1H-imidazole-1-propanamine | 13 | $1 \times 10^{-4}$ | 92 |
| 2-[[3-(1H-Imidazol-1-yl)propyl]imino]benz[cd]indole-1(2H)-pentanenitrile | 15 | $1 \times 10^{-4}$ | 94 |
| N-(1-Hexylbenz[cd]indol-2(1H)-ylidene)-1H-imidazole-1-propanamine, (E)-2-butenedioate (1:2) | 16 | $1 \times 10^{-4}$ | 94 |
| N-[1-(Phenylmethyl)benz[cd]indol-2(1H)-ylidene]-1H-imidazole-1-butanamine, (E)-2-butenedioate (1:2) | 23 | $1 \times 10^{-4}$ | 100 |
| N,N-Diethyl-2-[(3-pyridinylmethyl)imino]benz[cd]indol-1(2H)ethanamine, (E)-2-butenedioate (2:3) | 25 | $1 \times 10^{-4}$ | 91 |
| N-(1-Methylbenz[cd]indol-2(1H)-ylidene)-3-pyridinepropanamine, (E)-2-butenedioate (2:3) | 26 | $1 \times 10^{-4}$ | 93 |
| N-(1-Methylbenz[cd]indol-2(1H)-ylidene)-3-pyridinepropanamine, (E)-2-butenedioate (2:3) | 27 | $1 \times 10^{-4}$ | 100 |
| N-[1-(3-Pyridinylmethyl)benz[cd]indol-2(1H)-ylidene)-3-pyridinebutanamine, dihydrochloride | 31 | $1 \times 10^{-4}$ | 96 |
| 2-[[4-(3-Pyridinyl)butyl]imino]-benz[cd]indol-1(2H)-pentanenitrile, (E)-2-butenedioate (4:7) | 32 | $1 \times 10^{-4}$ | 98 |
| N-(1-Hexylbenz[cd]indol-2(1H)-ylidene)-3-pyridinebutanamine, (E)-2-butenedioate (2:3) | 33 | $1 \times 10^{-4}$ | 93 |
| N-[1-(Diphenylmethyl)benz[cd]indol-2(1H)-ylidene]-gamma-methyl-1H-imidazole-1-propanamine | 35 | $1 \times 10^{-4}$ | 88 |

The novel compounds of the present invention have been found to be highly useful for inhibiting thromboxane synthetase in mammals when administered in amounts ranging from about 1.0 mg to about 20.0 mg/kg of body weight per day. A preferred dosage regimen for optimum results would be from about 1.0 mg to about 10.0 mg/kg of body weight per day. Such dosage units are employed that a total of from about 70 to about 700 mg of active compound for a subject of about 70 kg of body weight are administered in a 24 hour period. This dosage regimen may be adjusted to provide the optimum therapeutic response. For example, several divided doses may be administered daily or the dose may be proportionally reduced as indicated by the exigencies of the therapeutic situation. The compounds of this invention are preferably administered orally but may be administered in any convenient manner such as by the intravenous, intramuscular, or subcutaneous routes.

The novel compounds of the present invention are active hypotensive agents and were tested for hypotensive activity by the method of P. S. Chan and D. Poorvin, Clinical and Experimental Hypertension, 1 (6), 817–830 (1979). Male, 16 week old, spontaneously hypertensive rats of the Okamoto strain, from Taconic Farms, Germantown, New York, having an average mean arterial blood pressure of 160±1.5 mm of mercury, were used in the test. One to 3 rats were used per test compound. A rat was dosed by gavage with a test compound suspended in 2% pre-boiled starch at a concentration of 50 mg/ml, at a dose of 100 mg/kg of body weight or less, with 0.9% sodium chloride loading at a dose of 25 ml/kg of body weight. A second identical dose of the test compound, without sodium chloride loading was given 24 hours later. At 28 hours after the initial dose the mean arterial blood pressure (MABP) was measured. The procedure was repeated in a second and third rat when necessary.

The results of this test on representative compounds of the present invention appear in Table II.

TABLE II

| Example No. | Compound | Hypotensive Activity Avg. MABP in mm Hg (No. of Rats) |
|---|---|---|
| 8 | N-[1-[2-(4-Morpholinyl)ethyl]-benz[cd]indol-2(1H)-ylidene]-1H-imidazole-1-propanamine, (E)-2-butenedioate (1:2) | 119 (2) |
| 12 | N-[1-(3-Phenoxypropyl)benz[cd]-indol-2(1H)-ylidene]-1H-imidazole-1-propanamine, dihydrochloride | 122 (4) |
| 14 | N-[1-[(3-Methoxyphenol)methyl]-benz[cd]indol-2(1H)-ylidene]-1H-imidazole-1-propanamine | 104 (2) |
| 22 | N-(1-Methylbenz[cd]indol-2(1H)-ylidene)-1H-imidazole-1-butanamine | 112 (2) |

TABLE II-continued

| Example No. | Compound | Hypotensive Activity Avg. MABP in mm Hg (No. of Rats) |
|---|---|---|
| 23 | N-[1-(phenylmethyl)benz[cd]indol-2(1H)-ylidene]-1H-imidazole-1-butanamine, (E)-2-butenedioate (1:2) | 124 (3) |
| 26 | N-(1-Methylbenz[cd]indol-2(1H)-ylidene)-3-pyridinepropanamine, (E)-2-butenedioate (2:3) | 114 (2) |
| 27 | N-(1-Methylbenz[cd]indol-2(1H)-ylidene)-3-pyridinepropanamine, (E)-2-butenedioate (2:3) | 107 (2) |
| 31 | N-[1-(3-Pyridinylmethyl)benz[cd]-indol-2(1H)-ylidene]-3-pyridine-butanamine, dihydrochloride | 119 (3) |
| 32 | 2-[[4-(3-Pyridinyl)butyl]imino]-benz[cd]indole-1(2H)-pentane-nitrile, (E)-2-butenedioate (4:7) | 129 (4) |
| 35 | N-[1-(Diphenylmethyl)benz[cd]-indol-2(1H)-ylidene]-gamma-methyl-1H-imidazole-1-propanamine | 127 (4) |

Intravenous administration of high doses of calcium or potassium chloride in animals produces cardiac arrhythmias, cardiac fibrillation and cardiac arrest. Any agent that can prevent these events is considered an antiarrhythmic/antifibrillatory agent. (Meth. and Find Exptl. Clin Pharmacal.2:223–252(1980); Pharmacol Ther. 24:401–433 (1984); Experimental Cardiac and Antiarrhythmic Drugs, L. Szekeres and Gy. J. Dapp, Akademiai Kiado Preso, Budapest, 9–448 (1971)).

The method employed is as follows: Male mice of the Swiss Webster Strain (Charles River, Wilmington, MA) weighing 25–35 g were anesthetized with ethyl carbamate (urethan) (1.5g/kg body weight i.p.). A 25-gauge needle attached to PE-20 tubing was inserted into a caudal vein for drug administration. The lead II ECG was recorded by needle electrodes placed subcutaneously in the limbs. All data were collected on a Gould Brush recorder. Animals were observed 5 minutes before drug administration. A 5, 15 or 30 minute period following drug administration was allowed before the bolus injection of calcium chloride, 200 mg/ kg i.v. or potassium chloride, 62.5 mg/kg i.v. Control mice received 4 ml/kg of 0.9% sodium chloride i.v. Mice were observed an additional 15 minutes for arrhythmias, fibrillation, survival or death. Any compound at a dose of less than 20 mg/kg i.v. in either test that protects from cardiac death 3 or more mice out of 6 mice, is considered active.

The results of this test on representative compounds of the present invention appear in Table III.

TABLE III

Antiarrhythmic/Antifibrillatory Activity of Chemicals in Anesthetized Mice

| Compound Dose = 10 mg/kg I.V. | Example No. | CaCl₂ Mice Surviving Mice Tested | KCl Mice Surviving Mice Tested |
|---|---|---|---|
| N-[1-(Phenylmethyl)benz[cd]indol-2(1H)-ylidene]-1H-imidazole-1-propanamine | 5 | 5/6 | 5/6 |
| N-[1-(Diphenylmethyl)benz[cd]indol-2(1H)-ylidene]-1H-imidazole-1-propanamine | 7 | 1/6 | 5/6 |
| N-[1-[2-(4-Morpholinyl)ethyl]benz[cd]indol-2(1H)-ylidene]-1H-imidazole-1-propanamine, (E)-2-butenedioate (1:2) | 8 | 0/6 | 5/6 |
| N-[1-[(3-Methoxyphenyl)methyl]benz[cd]indol-2(1H)ylidene]-1H-imidazole-1-propanamine | 14 | 1/6 | 4/6 |
| 2-[[3-(1H-Imidazol-1-yl)propyl]imino]benz- | 15 | 1/6 | 3/6 |

TABLE III-continued

Antiarrhythmic/Antifibrillatory Activity of Chemicals in Anesthetized Mice

| Compound Dose = 10 mg/kg I.V. | Example No. | CaCl$_2$ Mice Surviving Mice Tested | KCl Mice Surviving Mice Tested |
|---|---|---|---|
| [cd]indole-1(2H)-pentanenitile | | | |
| N,N-Diethyl-2-[[3-(1H-imidazol-1-yl)propyl]-imino]benz[cd]indole-1(2H)-ethanamine, (E)-2-butenedioate (1:3) | 17 | 1/6 | 4/6 |
| N-[1-Methylbenz[cd]indol-2(1H)-ylidene]-1H-imidazole-1-propanamine, (E)-2-butenedioate (1:2) | 18 | 0/6 | 4/6 |
| N,N'-[1,3-Propanediylbis(benz[cd]indol-1(2H)-ylidene)]bis-1H-imidazole-1-propanamine | 20 | 4/6 | 0/6 |
| 1,2-Dihydro-2-[[3-(1H-imidazol-1-yl)-propyl]-imino]-1-methylbenz[cd]indole-6-methanol, (E)-2-butanedioate (1:1) | 21 | 7/16 | 10/12 |
| N-[1-(Phenylmethyl)benz[cd]indol-2(1H)-ylidene]-1H-imidazole-1-butanamine, (E)-2-butenedioate (1:2) | 23 | 2/6 | 6/6 |
| N,N-Diethyl-2-[(3-pyridinylmethyl)imino]-benz[cd]indol-1(2H)ethanamine, (E)-2-butenedioate (2:3) | 25 | 1/6 | 3/6 |
| N-1(1-Methylbenz[cd]indol-2(1H)-ylidene)-3-pyridinepropanamine, (E)-2-butenedioate (2:3) | 26 | 2/12 | 4/12 |
| N-1-(1-Methylbenz[cd]indol-2(1H)-ylidene)-3-pyridinepropanamine, (E)-2-butenedioate (2:3) | 27 | 7/12 | 6/12 |
| N-[1-(Phenylmethyl)benz[cd]indol-2(1H)-ylidene]-3-pyridinebutanamine, (E)-2-butenedioate (1:2) | 29 | 2/6 | 4/6 |
| N-[1-Diphenylmethyl)benz[cd]indol-2(1H)-ylidene]-3-pyridinebutanamine | 30 | 1/6 | 5/6 |
| 2-[[4-(3-Pyridinyl)butyl]imino]benz-[cd]indole-1(2H)pentanenitrile, (E)-2-butenedioate (4:7) | 32 | 2/6 | 5/6 |
| N-[1-(Diphenylmethyl)benz[cd]indol-2(1H)-ylidene]-gamma-methyl-1H-imidazole-1-propanamine | 35 | 0/6 | 3/6 |
| Quinidine 15 mg/kg i.v. | — | 12/16 | 3/10 |
| Procainamide 5 mg/kg i.v. | — | — | 7/10 |
| Lidocaine 10 mg/kg i.v. | — | 5/6 | 5/10 |
| Control - Vehicle (Saline) | — | 0/75 | 0/75 |

Compositions according to the present invention having the desired clarity, stability and adaptability for parenteral use are obtained by dissolving from 0.10% to 10.0% by weight of active compound in a vehicle consisting of a polyhydric aliphatic alcohol or mixtures thereof. Especially satisfactory are glycerin, propylene glycol, and polyethylene glycols. The polyethylene glycols consist of a mixture of non-volatile, normally liquid, polyethylene glycols which are soluble in both water and organic liquids and which have a molecular weight of from about 200 to 1500. Although the amount of active compound dissolved in the above vehicle may vary from 0.10% to 10.0% by weight, it is preferred that the 15 amount of active compound employed be from about 3.0 to about 9.0% by weight. Although various mixtures of the aforementioned non-volatile polyethylene glycols may be employed, it is preferred to use a mixture having an average molecular weight of from about 200 to about 400.

In addition to the active compound, the parenteral solutions may also contain various preservatives which may be used to prevent bacterial and fungal contamination. The preservatives which may be used for these purposes are, for example, myristyl-gamma-picolinium chloride, benzalkonium chloride, phenethyl alcohol, p-chlorophenyl-glycerol ether, methyl and propyl parabens, and thimerosal. As a practical matter, it is also convenient to employ antioxidants. Suitable antioxidants include, for example, sodium bisulfite, sodium metabisulfite, and sodium formaldehyde sulfoxylate. Generally, from about 0.05 to about 0.2% concentrations of antioxidant are employed.

For intramuscular injection, the preferred concentration of active compound is 0.25 to 0.50 mg/ml of the finished compositions. The novel compounds of the present invention are equally adapted to intravenous administration when diluted with water or diluents employed in intravenous therapy such as isotonic glucose in appropriate quantities. For intravenous use, initial concentrations down to about 0.05 to 0.25 mg/ml of active ingredient are satisfactory.

The active compounds of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of tablets, troches, capsules, elixirs, suspensions, syrups, wafers, and the like. Such compositions and preparations should contain at least 0.1% of active compound. The percentage of the compositions and preparations may, of course, be varied and may conveniently be between about 2% to about 60% of the weight of the unit. The amount of active compound in such therapeutically useful compositions is such that a suitable dosage will be obtained.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier such as a fatty oil. Various other materials may be present as coatings or to otherwise modify the physical form of the dosage unit. For instance, tablets, pills or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed.

The following specific examples illustrate the preparation of the compounds of the present invention.

EXAMPLE 1

Preparation of 1-substituted benz[cd] indol-2(1H)-ones

The 1-substituted benz[cd]indol-2(1H)-ones (B) of this invention are prepared as exemplified by the following procedure for the synthesis of 1-[(4-methylphenyl)methyl]benz[cd]indol-2(1H)-one (Ba).

Eleven grams of 50% sodium hydride (in oil) is stirred with 250 ml of dry dimethylformamide, as 30 g benz[cd]indol-2(1H)-one is added in small portions. The reaction is stirred at room temperature for 2-2½ hours, then 25 g 4-methyphenylmethyl chloride is added and the reaction mixture is stirred at room temperature overnight. The reaction is concentrated in vacuo and treated with ice and dichloromethane with vigorous stirring.

The organic layer is dried over magnesium sulfate, passed through hydrous magnesium silicate, and concentrated giving 38.7 g of 1-[(4-methylphenyl)methyl]-benz[cd]indol-2(1H)-one, mp 108°-110°. (Ba) The following 1-substituted benz[cd]indol-2(1H)-ones are prepared substantially by the method described above:

(Bb) 1-Phenyl-benz[cd]indol-2(1H)-one mp. 100°-101° C., is made according to the procedure described in J of the Chemical Society, 1935, 317.

(Bc) 1-(Phenylmethyl)-benz[cd]indol-2(1H)-one, mp. 111°-113° C.

(Bd) 1-(Diphenylmethyl)-benz[cd]indol-2(1H)-one, mp. 161°-163° C.

(Be) 1-[2-(4-Morpholinyl)ethyl]-benz[cd]indol-2 (1H)-one, mp. 89°-93° C.

(Bf) 1-[3-(1-Piperidinyl)propyl]-benz[cd]indol-2 (1H)-one, oil.

(Bg) 1-(3-Pyridinylmethyl)-benz[cd]indol-2(1H)-one, mp. 118°-119° C.

(Bh) 1-[[3-Trifluoromethyl)phenyl]methyl-benz[cd]indol-2(1H)-one, mp. 57°-59° C.

(Bi) 1-(3-Phenoxypropyl)-benz[cd]indol-2(1H)-one, mp. 98°-100° C.

(Bj) 1-(3-Phenylpropyl)-benz[cd]indol-2(1H)-one, mp. 66°-67° C.

(Bk) 1-[(3-Methoxyphenyl)methyl]-benz[cd]indol-2 (1H)-one, mp. 68°-70° C.

(Bl) 2-Oxo-benz[cd]indol-1(2H)-pentanenitrile, oil.

(Bm) 1-Hexyl-benz[cd]indol-2(1H)-one, oil.

(Bn) 1-(2-Diethylaminoethyl)benz[cd]indol-2(1H)-one, HCl salt, mp. 195°-196° C.; (Bo) 1-methylbenz[cd]indol-2[1H]-one, mp. 77°-79° C.; (Bp) 1-(p-chlorophenyl methyl)benz[cd]indol-2(1H)-one, mp. 109°-111° C. are described in U.S. Pat. No. 4,261,896.

(Bq) 8-Methyl-1-(phenylmethyl)benz[cd]indol-2-(1H)-one mp 170°-171° C.

(Br) 6-Chloro-1-(phenylmethyl)benz[cd]indol-2(1H)-one mp 113°-114° C.

(Bs) 1,1'-(1,3-Propanediyl)bis-benz[cd]indol-2 (1H)-one:

Thirty four grams of benz[cd]indol-2(1H)-one is added with stirring to 500 ml of dry dimethylformamide. Ten grams of 50% sodium hydride (in oil) is added in portions, the reaction is stirred at room temperature for 1 hour, and then on a steam bath for one hour. A deep red/brown solution results. One hundred twenty grams of 1,3-dibromopropane is added in one portion, the red color disappears and a white suspension appears. The mixture is stirred and heated on a steam bath for 16 hours, concentrated to dryness and the residue dissolved in 250 ml of dichloromethane. The solution is passed through hydrous magnesium silicate and rinsed with 100 ml of dichloromethane; on standing at room temperature crystals formed. The solution is cooled to 0° C., collected and washed with 100 ml of hexane. After numerous fractional crystallizations, 12.6 g of (Bs) 1,1'-(1,3-propanediyl)bisbenz[cd]indol-2(1H)-one, mp. 161°-162° C. and (Bt) 1.4 g of 1-(3-bromopropyl)benz[cd]indol-2(1H)-one, mp. 74°-76° C., is obtained.

EXAMPLE 2

Preparation of 1-substituted benz[cd]indol-2(1H)-thiones

The synthesis of the title compounds is exemplified by the preparation of 1-[(4-methylphenyl)methyl]-benz[cd]indol-2(1H)-thione (Ca). Ten grams of 1-[(4-methylphenyl)methyl]benz[cd]indol-2(1H)-one (Ba) is dissolved in 80 ml of pyridine, 4.1 g of phosphorus pentasulfide is added and the mixture refluxed for 16 hours. The reaction mixture is poured into 1 liter of boiling water, heated for 10 minutes and allowed to cool to room temperature. The resulting precipitate is collected, dissolved in dichloromethane, washed with water, dried over sodium sulfate and concentrated in vacuo. A 1.5 g sample of the solid residue is recrystallized from dichloromethane/hexane giving 0.9 g of 1-[(4-methylphenyl)methyl]benz[cd]-indole-2(1H)-thione, mp. 144°-145° C. (Ca). The original solid residue is used for synthesis without further purification.

The following 1-substituted benz[cd]indole-2-(1H)-thiones are prepared from the corresponding 2-one derivatives of Example 1 by the method above or a slight modification of the method described:

(Cb) 1-Phenylbenz[cd]indole-2(1H)-thione, mp. 118°-120° C.

(Cc) 1-(Phenylmethyl)benz[cd]indole-2(1H)-thione, mp. 105°-106° C.

(Cd) 1-(Diphenylmethyl)benz[cd]indole-2(1H)-thione, mp. 195.5°-197.5° C.

(Ce) 1-[2-(4-Morpholinyl)ethyl]benz[cd]indole-2 (1H)-thione, orange solid.

(Cf) 1-[3-(1-Piperidinyl)propyl]benz[cd]indole-2(-1H)-thione, oil.

(Cg) 1-(3-Pyridinylmethyl)benz[cd]indole-2(1H)-thione, mp. 115°-116° C.

(Ch) 1-[[3-(Trifluoromethyl)phenyl]methyl]benz[cd]indole-2(1H)-thione, mp. 128°-129° C.

(Ci) 1-(3-Phenoxypropyl)benz[cd]indole-2[1H]-thione, mp. 127°-128° C.

(Cj) 1-(3-Phenylpropyl)benz[cd]indole-2[1H]-thione, mp. 82°-83° C.

(Ck) 1-[[3-Methoxyphenyl)methyl]benz[cd]indole-2(1H)-thione, mp. 91°-92° C.

(Cl) 2-Thioxobenz[cd]indole-1(2H)-pentanenitrile, mp. 67°-71° C.

(Cm) 1-Hexylbenz[cd]indole-2(1H)-thione, oil.

(Cn) 1-(2-Diethylaminoethyl)benz[cd]indole-2(1H)-thione, oil, (Co) 1-methylbenz[cd]indole-2(1H)-thione, mp. 126.5°-127.5° C.; and (Cp) 1-p-chlorophenylmethylbenz[cd]indole-2(1H)-thione, mp. 125°-126° C. are described in U.S. Pat. No. 4,261,896.

(Cq) 8-Methyl-1-(phenylmethyl)benz[cd]indole-2 (1H)-thione, mp 195°-196° C.

(Cr) 6-Chloro-1-(phenylmethyl)benz[cd]indole-2 (1H)-thione, mp 161°-162° C.

(Cs) 1,1'-(1,3-Propanediyl)bisbenz[cd]indole-2 (1H)-thione, mp. 184°-185° C.

(Cu) (6-Hydroxymethyl)-1-methylbenz[cd]indole-2 (1H)-thione:

Six grams of dry hydrogen chloride gas is bubbled into a suspension of 51 ml glacial acetic acid and 4.3 g paraformaldehyde. Eighteen and five-tenths grams of benz[cd]indole-2-thiol is added and the reaction stirred at 60° C. for 24 hours. To the resulting solid 700 mls of water is added; the precipitate is washed with water, saturated sodium bicarbonate solution and chloroform. The solid is recrystallized from boiling methanol giving 11.0 g of (6-hydroxymethyl)-1-methylbenz[cd]indol-2(1H)-thione (Cu), mp. 95°-97° C.

EXAMPLE 3

N-[1-[(4-Methylphenyl)methyl]benz[cd]indol-2(1H)ylidene]-1H-imidazole-1-propanamine A mixture of 2.5 g of 1-[(4-methylphenyl)methyl]-benz[cd]indole-2(1H)-thione (Ca) and 1.2 g of 1H-imidazole-1-propanamine in 200 ml of ethyl alcohol is stirred and heated. A 2.7 g portion of mercuric acetate is added, the mixture is stirred at reflux for 6 hours, cooled to room temperature and treated with 2N sodium hydroxide (pH 9). After filtering the solution through diatomaceous earth, the reaction is concentrated in vacuo. The resulting oil is dissolved in dichloromethane, washed neutral with water, dried over sodium sulfate and concentrated in vacuo. The crystalline residue is recrystallized from dichloromethane/hexane giving 2.2 g of the desired product, mp. 94°-95° C.

EXAMPLE 4

N-[1-Phenylbenz[cd]indol-2(1H)-ylidene]-1H-imidazole-1-propanamine

A mixture of 4.0 g of 1-phenylbenz[cd]indole-2(1H)-thione (Cb) and 2.1 g of 1H-imidazole-1-propanamine in 500 ml of ethyl alcohol is stirred and heated. A 4.9 g portion of mercuric acetate is added, the mixture is stirred at reflux for 6 hours, then filtered and the insolubles washed with 100 ml of ethyl alcohol. The combined filtrate and wash is taken to dryness in vacuo.

The residual oil is treated with 250 ml (2x) of boiling hexane, decanted and the oil cooled to −10° C. The resulting crystals are washed with cold hexane, dried in vacuo at room temperature, giving 2.55 g of the desired product, mp. 103°-105° C.

EXAMPLE 5

N-[1-(Phenylmethyl)benz[cd]indol-2 (1H)-ylidene]-1H-imidazole-1-propanamine

A mixture of 3.0 g 1-(phenylmethyl)benz[cd]indole-2(1H)-thione (Cc), 1.34 g of 1H-imidazole-1-propaneamine, 10.0 ml ethyl alcohol, and 3.5 g of mercuric acetate is reacted as described in Example 3, giving 2.6 g of the desired product, mp. 90°-93° C.

EXAMPLE 6

N-[1-(Phenylmethyl)benz[cd]indol-2(1H)-ylidene]-1H-imidazole-1-propanamine, (E)-2-butenedioate (1:2)

A mixture of 6.0 g of 1-(phenylmethyl)benz[cd]indole-2(1H)-thione (Cc), 2.8 g of 1H-imidazole-1-propanamine, 100 ml ethyl alcohol, and 7.0 g mercuric acetate is reacted as described in Example 3, giving 4.9 g of the desired product, mp. 90°-93° C. A solution of 4.9 g of product in 100 ml of acetone is treated with 3.2 g of fumaric acid in 300 ml of acetone with vigorous stirring. Three and nine-tenths gram of the difumarate salt is obtained, mp. 102°-104° C.

EXAMPLE 7

N-[1 (Diphenylmethyl)benz[cd]indol-2(1H)-ylidene]-1H-imidazole-1 propanamine

A mixture of 1.0 g of 1-(diphenylmethyl)benz[cd]indole-2(1H)-thione (Cd), 0.35 g of 1H-imidazole-1-propanamine, 20 ml ethyl alcohol and 0.91 g of mercuric acetate is reacted as described in Example 3, giving the desired product, mp. 142°-143° C.

EXAMPLE 8

N-[1-[2-(4-Morpholinyl)ethyl]benz[cd]indol-2(1H)-ylidene-1H-imidazole-1-propanamine, (E)-2-butenedioate (1:2)

A mixture of 1.1 g 1-[2-(4-morpholinyl)ethyl]benz[cd]indole-2(1H)-thione (Ce), 0.53 g of 1H-imidazole-1-propanamine, 45 ml of ethyl alcohol, and 1.37 g of mercuric acetate is reacted as described in Example 6, giving 1.74 g of the desired difumarate salt, mp. 133°-136° C.

EXAMPLE 9

N[1-[3-(1-Piperidinyl)propyl]benz[cd]indol-2(1H)-ylidene]-1H-imidazole-1-propanamine, (E)-2-butenedioate (2:7)

A mixture of 1.6 g of 1-[3-(1-piperidinyl)-propyl]-benz[cd]indole-2(1H)-thione (Cf), 0.74 g of 1H-imidazole-1-propanamine, 62 ml of pyridine, and 1.89 g of mercuric acetate is reacted as described in Example 6, giving 0.50 g of the desired fumarate salt, mp. 163°-165° C.

EXAMPLE 10

N[1-(3-Pyridinylmethyl)benz[cd]indol-2(1H)-ylidene-1H-imidazole-1-propanamine

A mixture of 2.75 g of 1-(3-pyridinylmethyl)-benz[cd]indole-2(1H)-thione (Cg), 1.4 g of 1H-imidazole -1-propanamine, 150 ml of ethyl alcohol and 3.5 g of mercuric acetate is reacted as described in Example 3, giving 2.7 g of the desired product, mp. 139°-141° C.

EXAMPLE 11

N-[1-[[3-(Trifluoromethyl)phenyl]methyl]benz[cd]indol 2(1H)-ylidene]-1H-imidazole-1-propanamine A mixture of 2.5 g of 1-[[3-(trifluoromethyl) phenyl]methyl]benz[cd]indole-2(1H)-thione (Ch), 0.95 g of 1H-imidazole-1-propanamine, 200 ml ethyl alcohol and 2.3 g of mercuric acetate is reacted as described in Example 3, giving 2.1 g of the desired product, mp. 108°–109° C.

EXAMPLE 12

N-[1-(3-Phenoxypropyl)benz[cd]indol-2(1H)-ylidene]-1H-imidazole-1-propanamine, dihydrochloride A mixture of 3.2 g of 1-(3-phenoxypropyl)benz[cd]indole-2(1H)-thione (Ci), 1.4 g of 1H-imidazole -1-propanamine, 150 ml ethyl alcohol, and 3.4 g of mercuric acetate is reacted as described in Example 3, giving 4.1 g of the desired product as an oil. A solution of 4.1 g of product in 100 ml of acetone is treated with 15 ml of 1.8N hydrochloric acid in ethyl alcohol with vigorous stirring. One and four-tenths gram of the desired dihydrochloride is obtained, mp. 193°–195° C.

EXAMPLE 13

N-[1-(3-Phenylpropyl)benz[cd]indol-2(1H)-ylidene]-1H-imidazole-1-propanamine, (E)-2-butenedioate (1:2)

A mixture of 3.0 g of 1-(3-phenylpropyl)benz[cd]indole-2(1H)-thione (Cj), 1.4 g of 1H-imidazole -1-propanamine, 75 ml of ethyl alcohol, and 3.5 g of mercuric acetate is reacted as described in Example 6, giving 5.1 g of the desired fumarate salt, mp. 169°–170° C. with decomposition.

EXAMPLE 14

N-[1-[(3Methoxyphenyl)methyl]benz[cd]indol-2(1H)-ylidene]-1H-imidazole-1-propanamine A mixture of 2.5 g of 1-[(3-methoxyphenyl)methyl]benz[cd]indole-2(1H)-thione (Ck), 1.1 g of 1H-imidazole-1-propanamine, 200 ml ethyl alcohol, and 2.6 g of mercuric acetate is reacted as described in Example 3, giving 2.6 g of the desired product, mp. 95°–96° C.

EXAMPLE 15

2-[[3-(1H-Imidazol-1 yl)propyl]imino]benz[cd]indole-1(2H)-pentanenitrile

A mixture of 4.0 g of 2-thioxobenz[cd]indole-1(2H)-pentanenitrile (Cl), 1.88 g of 1H-imidazole-1-propanamine, 100 ml of ethyl alcohol, and 4.8 g of mercuric acetate is reacted as described in Example 3, giving 4.3 g of the desired product, mp. 76°–78.5° C.

EXAMPLE 16

N-(1-Hexylbenz[cd]indol-2(1H)-ylidene)-1H-imidazole 1-propanamine, (E)-2-butenedioate (1:2)

A mixture of 3.0 g of 1-hexylbenz[cd]indole-2(1H)-thione (Cm), 1.39 g of 1H-imidazole-1-propanamine 100 ml ethyl alcohol, and 3.55 g of mercuric acetate is reacted as described in Example 6, giving 4.7 g of the desired fumarate salt, mp. 154°–157° C.

EXAMPLE 17

N,N-Diethyl-2-[[3-(1H-imidazol-1-yl)propyl]imino]-benz[cd]indole-1(2H)-ethanamine, (E)-2butenedioate (1:3)

A mixture of 2.0 g of 1-(2-diethylaminoethyl)benz[cd]indole-2(1H)-thione (Cn), 0.90 g of 1H-imidazole-1-propanamine, 50 ml of ethyl alcohol, and 2.2 g of mercuric acetate is reacted as described in Example 6, giving 1.5 g of the desired fumarate salt, mp. 116°–118° C.

EXAMPLE 18

N-[1-Methylbenz[cd]indol-2(1H)-ylidene]-1H-imidazole-1-propanamine, (E)-2-butenedioate (1:2)

A mixture of 6.0 g of N-[1-methylbenz[cd]indole]-2(1H)-thione (Co), 3.75 g of 1H-imidazole-1-propanamine, 400 ml of ethyl alcohol, and 7.5 g mercuric oxide is reacted as described in Example 6, giving 1.2 g of the desired fumarate salt, mp. 171°–172° C.

EXAMPLE 19

N-[1-[(4-Chlorophenyl)methyl]benz[cd]indol-2(1H)-ylidene]-1H-imidazole-1-propanamine A mixture of 2.5 g of 1-p-chlorophenylmethylbenz[cd]indole-2(1H)-thione (Cp), 1.1 g of 1H-imidazole -1-propanamine, 200 ml of ethyl alcohol, and 2.6 g of mercuric acetate is reacted as described in Example 3, giving 1.1 g of the desired product, mp. 90°–91° C.

EXAMPLE 20

N,N'-[1,3-Propanediylbis(benz[cd]indol-1(2H)-ylidene)]bis-1H-imidazole-1-propanamine A mixture of 2.4 g of 1,1'-(1,3-propanediyl) bisbenz[cd]indole-2(1H)-thione (Cs), 1.7 g of 1H-imidazole-1-propanamine, 450 ml of boiling ethyl alcohol, 125 ml of dimethylformamide, and 4.0 g of mercuric acetate is reacted as described in Example 3, giving 1.8 g of the desired product, mp. 152°–154° C.

EXAMPLE 21

1,2-Dihydro-2-[[3-(1H-imidazol-1-yl)propyl]imino]-1-methylbenz[cd]indole-6-methanol, (E)-2-butenedioate (1:1)

A mixture of 2.3 g of 6-(hydroxymethyl)-1-methylbenz[cd]indole-2(1H)-thione (Cu), 1.3 g of 1H-imidazole-1-propanamine, 100 ml of ethyl alcohol, and 3.5 g of mercuric acetate is reacted as described in Example 6, giving 3.0 g of the desired fumarate salt, mp. 153°–155° C. with decomposition.

EXAMPLE 22

N-(1-Methylbenz[cd]indol-2(1H)-ylidene)-1H-imidazole-1-butanamine

A mixture of 3.2 g of N-[1-methylbenz[cd]indole]-2(1H)-thione (Co), 2.5 g of 1H-imidazole-1-butanamine, 150 ml ethyl alcohol, and 5.1 g of mercuric acetate is reacted as described in Example 3, giving 1.8 g of the desired product, mp. 126°–127° C.

EXAMPLE 23

N-[1-(Phenylmethyl)benz[cd]indol-2(1H)-ylidene-1H-imidazole-1-butanamine,(E)-2-butenedioate (1:2)

A mixture of 3.0 g of 1-(phenylmethyl)benz[cd]indole-2(1H)-thione (Cc), 2.33 g of 1H-imidazole-1-butanamine, dihydrochloride, 1.2 g of sodium carbonate, 2.3 ml 10N sodium hydroxide, 100 ml ethyl alcohol and 3.5 g of mercuric acetate is reacted as described in Example 6, giving 2.1 g of the desired fumarate salt, mp. 105°-107° C.

EXAMPLE 24

N-[1-(Diphenylmethyl)benz[cd]indol-2(1H) ylidene-1H-imidazole-1-butanamine

A mixture of 3.5 g of 1-(diphenylmethyl)benz[cd]indole-2(1H)-thione(Cd), 1.4 g of 1H-imidazole-1-butanamine, 100 ml of ethyl alcohol and 3.2 g of mercuric acetate is reacted as described in Example 3, giving 1.86 g of the desired product, mp. 150°-152° C.

EXAMPLE 25

N,N-Diethyl-2-[(3-pyridinylmethyl)imino]benz[cd]indol-1(2H)ethanamine, (E)-2-butenedioate (2:3)

A mixture of 5.7 g of 1-(2-diethylaminoethyl)benz[cd]indole-2(1H)-thione (Cn), 2.4 g of 3-pyridinemethanamine, 300 ml ethyl alcohol, and 7.2 g of mercuric acetate is reacted as described in Example 6, giving 2.9 g of the desired fumarate salt, mp. 150°-151° C.

EXAMPLE 26

N-(1 Methylbenz[cd]indol-2(1H) -ylidene)-3-pyridinepropanamine, (E)-2-butenedioate (2:3)

A mixture of 5.3 g of N-[1-methylbenz[cd]indole]-2(1H)-thione (Co), 3.6 g of 3-pyridinepropanamine, 100 ml of ethyl alcohol, and 8.4 g of mercuric acetate is reacted as described in Example 6, giving 7.6 g of the desired fumarate salt, mp. 188°-189° C. with decomposition.

EXAMPLE 27

N-(1-Methylbenz[cd]indol-2(1H)-ylidene)-3-pyridinepropanamine, (E)-2-butenedioate (2:3)

A mixture of 6.0 g of N-[1-methylbenz[cd]indole]-2(1H)-thione (Co), 4.5 g of 3-pyridinebutanamine, 300 ml of ethyl alcohol, and 10 g of mercuric acetate is reacted as described in Example 6, giving 4.0 g of the desired fumarate salt, mp. 147°-149° C. with decomposition. cl EXAMPLE 28

N-(1 Phenylbenz[cd]indol 2(1H)-ylidene)-3-pyridinebutanamine, butanedioate (2:3)

A mixture of 4.0 g of 1-phenylbenz[cd]indole-2(1H)-thione (Cb), 2.5 g of 3-pyridinebutanamine, 500 ml of ethyl alcohol, and 4.9 g of mercuric acetate is reacted as described in Example 6, giving 3.0 g of the desired succinate salt, MH+ 378.

EXAMPLE 29

N-[1-(Phenylmethyl)benz[cd]indol-2(1H)-ylidene]-3-pyridinebutanamine, (E)-2 butenedioate (1:2)

A mixture of 3.0 g of 1-(phenylmethyl)benz[cd]indole-2(1H)-thione (Cb), 1.7 g of 3-pyridinebutanamine, 100 ml of ethyl alcohol, and 3.5 g of mercuric acetate is reacted as described in Example 6, giving 3.7 g of the desired fumarate salt, mp. 143°-144° C. with decomposition.

EXAMPLE 30

N-[1-Diphenylmethyl)benz[cd]indol-2(1H)-ylidene]-3-pyridinebutanamine

A mixture of 2.0 g of 1-(diphenylmethyl)benz[cd]indole-2(1H)-thione (Cd), 0.85 g of 3-pyridinebutanamine, 40 ml of ethyl alcohol, and 1.82 g of mercuric acetate is reacted as described in Example 3, giving the desired product, mp. 153°-156° C.

EXAMPLE 31

N-[1-(3-Pyridinylmethyl)benz[cd]indol 2(1H)-ylidene]-3-pyridinebutanamine, dihydrochloride A mixture of 3.5 g of 1-(3-pyridinylmethyl)benz[cd]indole-2(1H)-thione (Cg), 2.0 g of 3-pyridinebutanamine, 150 ml of ethyl alcohol, and 4.5 g of mercuric acetate is reacted as described in Example 12, giving 0.8 g of the desired hydrochloride salt, mp. 187°-189° C.

EXAMPLE 32

N2-[[4-(3-Pyridinyl)butyl]imino]benz[cd]indole-1(2H)-pentanenitrile, (E)2-butenedioate (4:7)

A mixture of 4.0 g of 2-thioxobenz[cd]indole1(2H)-pentanenitrile (Cl), 2.3 g of 3-pyridinebutanamine, 100 ml of ethyl alcohol, and 4.8 g of mercuric acetate is reacted as described in Example 6, giving 4.97 g of the desired fumarate salt, mp. 118°-121° C.

EXAMPLE 33

N-(1-Hexylbenz[cd]indol-2(1H)-ylidene)-3-pyridinebutanamine, (E)-2-butenedioate (2:3)

A mixture of 3.0 g of 1-hexylbenz[cd]indole2(1H)-thione (Cm), 1.7 g of 3-pyridinebutanamine, 100 ml of ethyl alcohol, and 3.55 g of mercuric acetate is reacted as described in Example 6, giving the desired fumarate salt, mp. 109°-119° C.

EXAMPLE 34

N-[1-(Diphenylmethyl)benz[cd]indol 2(1H)-ylidene]beta-methyl-1H-imidazole-1-propanamine A mixture of 3.51 g 1-(diphenylmethyl)benz[cd]indole-2(1H)-thione (Cd), 1.39 g of 1H-imidazole-1-propanamine-beta-methyl, 100 ml of ethyl alcohol, and 3.2 g of mercuric acetate is reacted as described in Example 3, giving 3.5 g of the desired product as a glass, mp. 51°-56° C.

EXAMPLE 35

N-[1-(Diphenylmethyl)benz[cd]indol-2(1H)-ylidene]alpha-methyl-1H-imidazole-1-propanamine A mixture of 3.5 g of 1-(diphenylmethyl)benz[cd]indole-2(1H)-thione (Cd), 1.4 g of 1H-imidazole-1-propanamine-alpha-methyl, 100 ml of ethyl alcohol, and 3.2 g of mercuric acetate is reacted as described in Example 3, giving 2.7 g of the desired product, mp. 55°-64° C.

EXAMPLE 36

N-[8-Methyl-1-(phenylmethyl)benz[cd]indol-2(1H)-ylidene]-1H-imidazole-1-propanamine A mixture of 2.9 g of (8-methyl-1-(phenylmethyl)-benz[cd]indole-2(1H)-thione (Cq), 1.4 g of 1H-imidazole-1-propanamine, 250 ml of ethanol, 50 ml of dimethylformamide, and 3.5 g of mercuric acetate is reacted as described in Example 3, giving 1.6 g of the desired product, mp 107°-109° C.

EXAMPLE 37

N-[6-Chloro-1-(phenymethyl)benz[cd]indol-2(1H)-ylidene]-1H-imidazole-1-propanamine A mixture of 3.1 g of 6-chloro-1-(phenylmethyl)-benz[cd]indole-2(1H)-thione (Cr), 1.4 g of 1H-imidazole-1-propanamine, 250 ml of ethanol, 75 ml of dimethylformamide, and 3.5 g of mercuric acetate is reacted as described in Example 3, giving 2.6 g of the desired product, mp 147°-149° C.

EXAMPLE 38

N-[6-Chloro-1-(phenylmethyl}benz[cd]indol 2(1H)-ylidene-(3-pyridine)ethanamine

A mixture of 3.1 g of 6-chloro-1-(phenylmethyl)-benz[cd]indole-2(1H)-thione (Cr), 1.5 g of (3-pyridine)ethanamine, 350 ml of ethanol, 50 ml of dimethylformamide, and 3.5 g of mercuric acetate is reacted as described in Example 3, giving 1.6 g of the desired product, mp 108°-110° C.

EXAMPLE 39

N-[8-Methyl-1-(phenylmethyl)benz[cd]indol-2(1H)-ylidene]-(4-pyridine)butanamine

A mixture of 2.6 g of 8-methyl-1-(phenylmethyl)-benz[cd]indole-2(1H)-thione (Cq), 1.5 g of (4-pyridine)-butanamine, 350 ml of ethanol, 50 ml of dimethylformamide, and 3.2 g of mercuric acetate is reacted as described in Example 3, giving 1.9 g of the desired product, mp 121°-123° C.

EXAMPLE 40

N-(1-Phenylbenz[cd]indol-2(1H)-ylidene)(2-pyridine)-thanamine

A mixture of 1.6 g of 1-phenylbenz[cd]indole-2(1H)-thione (Cb), 0.8 g of 2-(2-pyridine)ethanamine, 400 ml of ethanol and 2.5 g of mercuric acetate is reacted as described in Example 3, giving 0.8 g of the desired product, mp 95°-96° C.

We claim:

1. A compound having the formula:

wherein $R_1$ is selected from the group consisting of alkyl $C_1$-$C_6$, phenyl, phenylalkyl ($C_1$-$C_3$), phenoxyalkyl ($C_1$-$C_3$), X = CH$_3$O—
CF$_3$—
halogen $R_2$ is selected from the group consisting of hydrogen, HOCH$_2$—, or halogen; Q is selected from the group consisting of —(CH$_2$)$_n$, where n is an integer 1–4, straight or branched chain alkyl $C_1$-$C_4$; $R_3$ is selected from the group consisting of:

$R_4$ is selected from the group consisting of hydrogen or methyl or a pharmacologically acceptable salt thereof.

2. The compound according to claim 1, N-[1-[(4-methylphenyl)methyl]benz[cd]indol-2(1H)-ylidene]-1H-imidazole-1-propanamine.

3. The compound according to claim 1, N-[1-phenylbenz[cd]indol-2(1H)-ylidene]-1H-imidazole-1-propanamine.

4. The compound according to claim 1, N-[1-(phenylmethyl)benz[cd]indol-2(1H)-ylidene]-1H-imidazole-1-propanamine.

5. The compound according to claim 1, N-[1-(phenylmethyl)benz[cd]indol-2(1H)-ylidene]-1 H-imidazole-1-propanamine, (E)-2-butenedioate (1:2).

6. The compound according to claim 1, N-[1-(diphenylmethyl)benz[cd]indol-2(1H)-ylidene]-1H-imidazole1-propanamine.

7. The compound according to claim 1, N-[1-[2-(4-morpholinyl)ethyl]benz[cd]indol-2(1H)-ylidene]-1H-imidazole-1-propanamine, (E)-2-butenedioate (1:2).

8. The compound according to claim 1, N-[1-[3-(1-piperidinyl)propyl]benz[cd]indol-2(1H)-ylidene]-1H-imidazole-1-propanamine, (E)-2-butenedioate (2:7).

9. The compound according to claim 1, N-[1-(3-pyridinylmethyl)benz[cd]indol-2(1H)-ylidene]-1H-imidazole-1-propanamine.

10. The compound according to claim 1, N-[1-[[3-trifluoromethyl)phenyl]methyl]benz[cd]indol-2-(1H)-ylidene]-1H-imidazole-1-propanamine.

11. The compound according to claim 1, N-[1-(3-phenoxypropyl)benz[cd]indol-2(1H)-ylidene]-1H-imidazole-1-propanamine, dihydrochloride.

12. The compound according to claim 1, N-[1-(3-phenylpropyl)benz[cd]indol-2(1H)-ylidene]-1H-imidazole-1-propanamine, (E)-2-butenedioate (1:2).

13. The compound according to claim 1, N-[1-[(3-methoxyphenyl)methyl]benz[cd]indol-2(1H)-ylidene]-1H-imidazole-1-propanamine.

14. The compound according to claim 1, 2-[[3-(1H-imidazol-1-yl)propyl]imino]benz[cd]indole-1 (2H)-pentanenitrile.

15. The compound according to claim 1, N-(1-hexylbenz[cd]indol-2(1H)-ylidene)-1H-imidazole-1-propanamine, (E)-2-butenedioate (1:2).

16. The compound according to claim 1, N,N-diethyl-2-[[3-(1H-imidazol-1-yl)propyl]imino]benz[cd]indole-1(2H)-ethanamine, (E)-2-butenedioate (1:3).

17. The compound according to claim 1, N-[1-methylbenz[cd]indol-2(1H)-ylidene]-1H-imidazole-1-propanamine, (E)-2-butenedioate (1:2).

18. The compound according to claim 1, N-[1-[(4-chlorophenyl)methyl]benz[cd]indol-2(1H)-ylidene]-1H-imidazole-1-propanamine.

19. The compound according to claim 1, N,N'-[1,3-propanediylbis(benz[cd]indol-1(2H)-yl-2-ylidene)]bis-1H-imidazole-1-propanamine.

20. The compound according to claim 1, 1,2-dihydro-2-[[3-(1H-imidazol-1-yl)propyl]imino]-1-methylbenz[cd]indole-6-methanol, (E)-2-butenedioate (1:1).

21. The compound according to claim 1, N-(1-methylbenz[cd]indol-2(1H)-ylidene)-1H-imidazole-1-butanamine.

22. The compound according to claim 1, N-[1-(phenylmethyl)benz[cd]indol-2(1H)-ylidene]-1H-imidazole-1-butanamine, (E)-2-butenedioate (1:2).

23. The compound according to claim 1, N-[1-(diphenylmethyl)benz[cd]indol-2(1H)-ylidene]-1H-imidazole-1-butanamine.

24. The compound according to claim 1, N,N-diethyl-2-[(3-pyridinylmethyl)imino]benz[cd]indol-1(2H)-ethanamine, (E)-2-butenedioate (2:3).

25. The compound according to claim 1, N-(1-methylbenz[cd]indol-2(1H)-ylidene)-3-pyridinepropanamine, (E)-2-butenedioate (2:3).

26. The compound according to claim 1, N-(1-methylbenz[cd]indol-2(1H)-ylidene)-3-pyridinepropanamine, (E)-2-butenedioate (2:3).

27. The compound according to claim 1, N-(1-phenylbenz[cd]indol-2(1H)-ylidene)-3-pyridinebutanamine, butanedioate (2:3).

28. The compound according to claim 1, N-[1-(phenylmethyl)benz[cd]indol-2(1H)-ylidene]-3-pyridinebutanamine, (E)-2-butenedioate (1:2).

29. The compound according to claim 1, N-[1-(diphenylmethyl)benz[cd]indol-2(1H)-ylidene]-3-pyridinebutanamine.

30. The compound according to claim 1, N-[1-(3-pyridinylmethyl)benz[cd]indol-2(1H)-ylidene]-3-pyridinebutanamine, dihydrochloride.

31. The compound according to claim 1, 2-[[4-(3-pyridinyl)butyl]imino]benz[cd]indole-1-(2H)-pentanenitrile, (E)-2-butenedioate (4:7).

32. The compound according to claim 1, N-(1-hexylbenz[cd]indol-2(1H)-ylidene)-3-pyridinebutanamine, (E)-2-butenedioate (2:3).

33. The compound according to claim 1, N-[1-(diphenylmethyl)benz[cd]indol-2(1H)-ylidene]-betamethyl-1H-imidazole-1-propanamine.

34. The compound according to claim 1, N-[1-(diphenylmethyl)benz[cd]indol-1-(1H)-ylidene]gamma-methyl-1H-imidazole-1-propanamine.

35. The compounds according to claim 1, N-[8-methyl-1-(phenylmethyl)benz[cd]indol-2(1H)-ylidene]-1H-imidazole-1-propanamine.

36. The compound according to claim 1, 1-[6-chloro-1-(phenylmethyl)benz[cd]indol-2(1H)-ylidene]-1H-imidazole-1-propanamine.

37. The compound according to claim 1, N-[6-chloro-1-(phenylmethyl)benz[cd]indol-2-(1H)-ylidene]-(3-pyridine)ethanamine.

38. The compound according to claim 1, N-[8-methyl-1-(phenylmethyl)benz[cd]indol-2(1H)-ylidene]-(4-pyridine)butanamine.

39. The compound according to claim 1 N-(1-phenybenz[cd]indol-2(1H)-ylidene)-(2-pyridine) ethanamine.

40. The method of inhibiting thromboxane synthetase enzyme in a mammal which comprises administering internally to said mammal a thromboxane synthetase enzyme inhibiting amount of a compound of claim 1.

41. The method of inhibiting hypertension in a mammal which comprises administering to said mammal a hypotensive inhibiting amount of a compound of claim 1.

42. The method of inhibiting arrhythmia in a mammal which comprises administering internally to said mammal an arrhythmia inhibiting amount of a compound of claim 1.

43. A pharmaceutical composition of matter in dosage unit form comprising from about 1 to about 700 mg of a compound selected from those of claim 1 in association with a pharmaceutically acceptable carrier.

* * * * *